United States Patent [19]  [11] 4,099,956
Pilgram  [45] Jul. 11, 1978

[54] HERBICIDAL SEMICARBAZONES

[75] Inventor: Kurt H. G. Pilgram, Modesto, Calif.

[73] Assignee: Shell Oil Company, Houston, Tex.

[21] Appl. No.: 732,678

[22] Filed: Oct. 15, 1976

Related U.S. Application Data

[63] Continuation-in-part of Ser. No. 466,103, May 20, 1974, which is a continuation of Ser. No. 283,686, Aug. 25, 1972, abandoned.

[51] Int. Cl.$^2$ .............................................. A01N 9/20
[52] U.S. Cl. ...................................... 71/120; 260/554
[58] Field of Search .......................... 71/120; 260/554

[56]  References Cited
U.S. PATENT DOCUMENTS

| | | | |
|---|---|---|---|
| 2,261,735 | 11/1971 | Gertler et al. | 260/554 |
| 2,655,445 | 10/1953 | Todd | 71/120 |
| 3,165,549 | 1/1965 | Martin et al. | 71/120 |
| 3,318,680 | 5/1967 | Levitt | 71/120 |
| 3,382,061 | 5/1968 | Bondarenko et al. | 71/120 |
| 3,439,018 | 4/1969 | Brookes et al. | 71/120 |
| 3,709,936 | 1/1973 | Fridinger et al. | 260/554 |
| 3,712,914 | 1/1973 | Tilles | 71/120 |
| 3,734,961 | 5/1973 | Englehart | 71/120 |
| 3,829,486 | 8/1974 | Baker | 260/554 |

FOREIGN PATENT DOCUMENTS

| | | | |
|---|---|---|---|
| 44-29,874 | 3/1969 | Japan | 71/120 |
| 7,010,689 | 1/1972 | Netherlands | 71/120 |

*Primary Examiner*—Glennon H. Hollrah

[57]  ABSTRACT

2-Phenylsemicarbazones of the formula

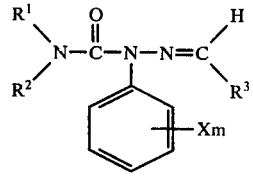

wherein $R^1$ and $R^2$ are alkyl; $R^3$ is H, alkyl, or alkenyl; X is halogen, trifluoromethyl, cycloalkylalkoxy or alkoxy and $m$ is 1 or 2 are useful as herbicides.

7 Claims, No Drawings

HERBICIDAL SEMICARBAZONES

CROSS-REFERENCE TO RELATED APPLICATIONS

This application is a continuation-in-part of Ser. No. 466,103, filed May 20, 1974, which is a continuation-in-part of Ser. No. 283,686, filed Aug. 25, 1972, now abandoned.

BACKGROUND OF THE INVENTION

1. Field of the Invention

This invention relates to new herbicides and to herbicidal compositions containing said herbicides. More specifically, this invention relates to a new class of 2-phenylsemicarbazones, and to a new method for controlling undesirable plant growth using said 2-phenylsemicarbazones.

2. Description of the Prior Art

Netherlands application No. 6,900,033 discloses certain derivatives of 1,2-dicarbonylphenylhydrazones, useful as insecticides and acaricides. Netherlands application No. 7,010,689 discloses benzaldehyde 2-(3,4-dichlorophenyl)-4,4-dimethylsemicarbazone as an intermediate for herbicides.

SUMMARY OF THE INVENTION

The novel compounds of this invention are respresented by the formula

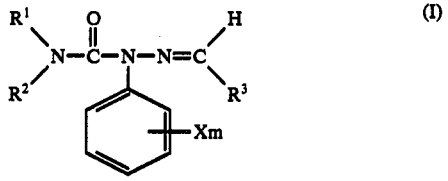

(I)

where $R^1$ and $R^2$ are each alkyl; $R^3$ is hydrogen, alkyl, or alkenyl; X is halogen, trifluoromethyl, cycloalkylalkoxy, or alkoxy; and $m$ is 1 or 2.

Herbicidal compositions of this invention comprise a compound within the scope of the invention and an inert agriculturally acceptable carrier therefor. Undesirable plant growth is destroyed or prevented by applying the compounds of the invention, ordinarily in a herbicidal composition of one of the aforementioned types, to either the unwanted growth itself or to the area to be kept free of such unwanted growth.

The 2-phenylsemicarbazones are also useful as intermediates for certain herbicidal 2-phenylsemicarbazides. For a more detailed description of these 2-phenylsemicarbazides, see Serial No. 283,687, filed August 25, 1972, the disclosure of which is hereby incorporated by reference.

DETAILED DESCRIPTION OF THE INVENTION

Typical novel compounds of this invention are those of Formula I above wherein $R^1$ and $R^2$ are each alkyl of 1 to 4 carbon atoms, for example, methyl, ethyl, isopropyl, tert-butyl, and the like; $R^3$ is hydrogen, alkyl of 1 to 4 carbon atoms, for example, methyl, ethyl, isopropyl, butyl and the like or alkenyl of 2 to 5 carbon atoms, for example, propenyl; X is halogen or atomic number 9 to 35 inclusive, preferably chlorine or fluorine, trifluoromethyl, cycloalkylalkoxy of 3 to 6 ring carbon atoms, for example cyclopropylmethoxy or cyclopropyle-thoxy or alkoxy wherein the alkyl portion contains 1 to 5 carbon atoms and can be straight- or branched-chain, for example, isopropoxy and the like; and $m$ is 1 or 2, preferably 2. The substituents X are preferably located at the 3- and/or 4-position on the phenyl ring.

Typical compounds contemplated for use within the scope of this invention are:
formaldehyde, 2-(3-(trifluoromethyl)-4-chlorophenyl)-4,4-dimethylsemicarbazide.
propionaldehyde, 2-(3-(trifluoromethyl)-4-isopropoxyphenyl)-4,4-dimethylsemicarbazide.

Preferred because of their especially effective herbicidal properties and their ability to control weeds at relatively low dosages are those semicarbazones of Formula I wherein $R^1$ and $R^2$ are each methyl; $R^3$ is hydrogen, alkyl of 1 to 4 carbon atoms, especially isopropyl, or alkenyl of 2 to 5 carbon atoms, especially propenyl; $m$ is 2 and one of X is halogen or trifluoromethyl while the other is branched-chain alkoxy or halogen. Preferred are compounds where $m$ is 2 and the two X substituents 3-chloro and 4-fluoro.

A suitable method for preparing the 2-phenylsemicarbazones comprises converting a 2-phenylsemicarbazone of one specific aldehyde into a 2-phenyl-semicarbazone of a different aldehyde by hydrolyzing the initially prepared 2-phenylsemicarbazone into the corresponding 2-phenylsemicarbazide which is then reacted with the desired aldehyde. For example, benzaldehyde 2-(3-chloro-4-fluorophenyl)-4,4-dimethylsemicarbazone prepared e.g., from benzaldehyde 3-chloro-4-fluorophenylhydrazone and dimethylcarbamoyl chloride is hydrolyzed to 2-(3-chloro-4-fluorophenyl)-4,4-dimethylsemicarbazide which is reacted with formaldehyde to give formaldehyde 2-(3-chloro-4-fluorophenyl)-4,4-dimethylsemicarbazone.

Compounds of this invention, for example, formaldehyde 2-(3-chloro-4-fluorophenyl)-4,4-dimethylsemicarbazone; formaldehyde 2-(3-chloro-4-isopropoxyphenyl)-4,4-dimethylsemicarbazone, and crotonaldehyde 2-(3-chloro-4-isopropoxyphenyl)-4,4-dimethylsemicarbazone have been found to be active herbicides of a general type. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes herbicidal compositions comprising a carrier or a surface-active agent, or both a carrier and a surface-active agent, and, as active ingredient, at least one 2-phenylsemicarbazone of Formula I. Likewise, the invention also includes a method of combatting weeds which comprises applying to the locus a herbicidally effective amount of a 2-phenylsemicarbazone or composition of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax and chlorinated mineral waxes; and solid fertilizers, for example, superphosphates.

Examples of suitable fluid carriers are water, alcohols, such as for example, isopropanol, glycols; ketones, such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium of calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 1-5% of surface active agent and where necessary, 0-15% by weight of stabilizer(s) and/or other additives such as penetrants or stickers. Dusts are usually formulated as a dust concentrate having a similar composition to that of a wettable powder but without a dispersant or surface active agent, and are diluted in the field with further solid carrier to give a composition usually containing ½-10% by weight of toxicant. Granules are usually prepared to have a size between 10 and 100 BS mesh (1.676-0.152 mm), and may be manufactured by agglomeration or impregnation techniques. Generally granules will contain ½-25% by weight toxicant and 0-10% by weight of additives such as stabilizers, slow release modifiers and binding agents. Emulsifiable concentrates usually contain, in addition to the solvent, and when necessary, co-solvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% w toxicant, 0.5-5% w of dispersing agents, 1-5% of surface active agent, 0.1-10% w of suspending agents such as protective colloids and thixotropic agents, 0-10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compositions of this invention comprises applying a 2-phenylsemicarbazone, ordinarily in a herbicidal composition of one of the aforementioned types, to a locus or area to be protected from undesirable plant growth. The active compound of course is applied in amounts sufficient to exert the desired herbicidal action.

The amount of the 2-phenylsemicarbazone to be used in controlling undesirable vegetation will naturally depend on the condition of the vegetation, the degree of herbicidal activity desired, the formulation used, the mode of application, the climate, the season of the year, and other variables. Recommendations as to precise amounts are, therefore, not possible. In general, however, application to the locus to be protected of from 0.1 to 10 pounds per acre of the herbicidal compounds used in this invention will be satisfactory.

The preparation and some of the properties of the novel 2-phenylsemicarbazones of the invention are illustrated by the following examples. It should be understood, however, that the examples given are for the purpose of illustration only, and are not to be regarded as limiting the invention in any way. In the examples below, the structure of all the products prepared was confirmed by elemental, nuclear magnetic resonance, and infrared analyses.

EXAMPLE 1

To a solution of 54.3 g of 2-(3-chloro-4-fluorophenyl)-4,4-dimethylsemicarbazide in 300 ml of benzene was added rapidly 40.5 g of 37% formaldehyde, followed by 240 g of $Mg_2SO_4$ at ambient temperature. After several days, an additional 40 g of 37% formaldehyde was added and the mixture was stirred for 18 hours. The resulting product was filtered and the filtrate was concentrated to dryness leaving an amber syrup which was purified by silica chromatography to yield 4.5 g of formaldehyde 2-(3-chloro-4-fluorophenyl)-4,4-dimethylsemicarbazone as a viscous oil.

EXAMPLE 2

To a solution of 10 g of 2-(3-chloro-4-isopropoxyphenyl)-4,4-dimethylsemicarbazide in 50 ml of benzene was added 2.6 g of crotonaldehyde and a catalytic amount of p-toluenesulfonic acid. The mixture was heated to reflux for 4 hours. The solvent was removed in vacuo leaving 11.7 g of crotonaldehyde 2-(3-chloro-4-isopropoxyphenyl)-4,4-dimethylemicarbazone as a yellow-brown, viscous oil.

EXAMPLES 3 – 11

Using the experimental procedures similar to those used in Examples 1 and 2, the compounds of Table I were prepared.

Table I

2-Phenylsemicarbazones

| Example No. | $R^1$ | $R^2$ | $R^3$ | Xm |
|---|---|---|---|---|
| 3 | $CH_3$ | $CH_3$ | $(CH_3)_2CH-$ | 3-Cl,-4-F |
| 4 | $CH_3$ | $CH_3$ | $CH_3CH=CH-$ | 3-Cl,4-F |
| 5 | $CH_3$ | $CH_3$ | H | 3-Cl,4-isopropoxy |
| 6 | $CH_3$ | $CH_3$ | $C_2H_5$ | 3-Cl,4-isopropoxy |
| 7 | $CH_3$ | $CH_3$ | $C_2H_5$ | 3-$CF_3$-4-F |

The above compounds were all highly viscous oils which showed no tendency to crystallize.

EXAMPLE 12

The pre-emergence herbicidal activity of the compounds of the invention was evaluated by planting seeds of watergrass, cress, downey brome, velvet leaf, yellow foxtail, sicklepod, cotton, grain sorghum, soybean and wheat in soil treated with the test compounds at the rates of 1 and 0.1 mg per tube designated in Table II as Rates I an II, respectively. The planted soil was held under controlled conditions of temperature, moisture, and light for 13 to 14 days. The amount of germination was then noted and the effectiveness of the test compound was rated on the basis of an 0 to 9 scale, 0 rating indicating no effect, 9 indicating death of the seedlings or no germination.

The post-emergence activity of the compounds of this invention was evaluated by spraying 7-day old crabgrass plants, 10-day old pigweed plants, 7-day old downey brome plants, 10-day old velvet leaf plants, 10-day old yellow foxtail plants, 8-day old sicklepod plants, 14-day old cotton plants, 7-day old grain sorghum plants, 14-day old soybean plants and 7-day old wheat plants, with a liquid formulation of the test compound at the rates of 0.5 and .05% solutions weight to volume, designated in Table II as Rates I and II, respectively. The sprayed plants were held under controlled conditions for 10 to 11 days and the effect of the test chemical was then evaluated visually, the results being rated on the 0 to 9 scale described above.

The results of the tests are summarized in Table II.

TABLE II

HERBICIDAL ACTIVITY

| | PRE-EMERGENCE (SOIL) | | | | | | | | | | | | | | | | | | POST-EMERGENCE (FOLIAR) | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| | Water-grass | | Garden Cress | | Downey Brome | | Velvet Leaf | | Yellow Foxtail | | Sickle-pod | | Cotton | | Grain Sorghum | | Soybean | | Wheat | | Crab-grass | | Pig-weed | | Downey Brome | | Velvet Leaf | | Yellow Foxtail | | Sickle-pod | | Cotton | | Grain Sorghum | | Soybean | | Wheat |
| Example | I | II | I | II | I | II | I | II | I | II | I | II | II | II | II | II | I | II | I | II | I | II | I | II | I | II | I | II | I | II | II | II | II |
| 1 | — | 9 | 4 | 8 | 7 | — | — | 8 | 7 | 0 | 2 | 1 | 1 | — | 0 | — | 7 | — | 3 | 3 | — | 5 | 3 |
| 2 | 6 | 9 | 7 | 9 | 9 | 0 | 0 | 9 | 8 | 8 | 7 | 6 | 2 | 6 | 8 | 9 | 4 | 0 | 2 | 2 | 2 | 2 | 0 |
| 3 | 5 | 8 | 6 | 8 | 6 | 6 | 9 | 9 | 6 | 7 | 6 | 7 | 8 | 9 | 4 | 2 | 8 | 0 | 2 | 2 | 0 | 2 | 2 |
| 4 | 2 | 9 | 2 | 7 | 1 | 8 | 8 | 7 | 0 | 4 | 6 | 1 | 3 | 9 | 9 | 7 | 4 | 8 | 2 | 9 | 5 | 9 | 5 | 6 | 6 | 0 |

I claim:
1. A compound of the formula

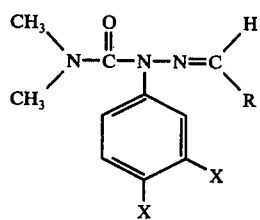

wherein R is hydrogen, alkyl of 1 to 5 carbon atoms or alkenyl of 2 to 5 carbon atoms and one of X is halogen of atomic number 9 to 35 inclusive, or trifluoromethyl and the other is halogen or alkoxy in which the alkyl portion is straight or branched chain and contains from 1 to 4 carbon atoms.

2. A compound according to claim 1 wherein one of X is halogen and the other is branched-chain alkoxy.

3. A compound according to claim 2 wherein one X is chlorine and the other is isopropoxy.

4. A compound according to claim 1 wherein each X is halogen.

5. A compound according to claim 4 wherein one X is chlorine and the other X is fluorine.

6. A herbicidal composition comprising a herbicidally effective amount of a compound as claimed in claim 1 and an inert, agriculturally acceptable carrier therefor.

7. A method for controlling undesirable plant growth at a locus to be protected comprising applying to the locus an herbicidally effective amount of a compound as claimed in claim 1.